United States Patent
Cardozo et al.

(10) Patent No.: US 7,026,301 B2
(45) Date of Patent: Apr. 11, 2006

(54) METHOD OF ORALLY TREATING INFLAMMATORY SKIN CONDITIONS WITH PRODRUGS OF 5-FLUOROURACIL

(75) Inventors: Timothy J. Cardozo, New York, NY (US); John C. Pui, Ann Arbor, MI (US)

(73) Assignee: New York University, New York, NY (US)

( * ) Notice: Subject to any disclaimer, the term of this patent is extended or adjusted under 35 U.S.C. 154(b) by 140 days.

(21) Appl. No.: 10/689,530

(22) Filed: Oct. 17, 2003

(65) Prior Publication Data

US 2005/0085438 A1    Apr. 21, 2005

Related U.S. Application Data

(60) Provisional application No. 60/419,231, filed on Oct. 17, 2002.

(51) Int. Cl.
*A61K 3/7072* (2006.01)
*A61K 3/513* (2006.01)

(52) U.S. Cl. .......... 514/50; 514/49; 514/283; 514/274; 514/27; 514/251; 514/252.02; 514/24; 514/34; 514/256; 514/300; 514/44; 514/302; 514/403; 536/24.5; 536/23.1; 536/24.31; 536/24.33; 536/24.1; 536/24.3; 536/23.2; 435/375; 435/377; 435/91.1; 435/6; 435/324; 435/366; 435/320.1; 435/91.3; 435/325; 424/93.21; 424/155.1

(58) Field of Classification Search .......... 514/50, 514/49, 283, 274, 27, 251, 252.02, 24, 34, 514/256, 300, 44, 302, 403; 536/24.5, 23.1, 536/24.31, 24.33, 24.1, 24.3, 23.2; 435/375, 435/377, 91.1, 6, 324, 366, 320.1, 91.3, 325; 424/93.21, 155.1
See application file for complete search history.

(56) References Cited

U.S. PATENT DOCUMENTS

| | | | | |
|---|---|---|---|---|
| 5,654,286 A | * | 8/1997 | Hostetler | 514/47 |
| 5,922,714 A | | 7/1999 | Hausheer | |
| 6,297,223 B1 | * | 10/2001 | Spector et al. | 514/50 |
| 6,664,242 B1 | * | 12/2003 | Bissery | 514/49 |

* cited by examiner

*Primary Examiner*—James O. Wilson
*Assistant Examiner*—Devesh Khare
(74) *Attorney, Agent, or Firm*—Darby & Darby

(57) ABSTRACT

The present invention relates to the treatment of inflammatory skin conditions, including psoriasis, with a prodrug of 5-fluorouracil. The invention relates to methods for treatment of psoriasis with capecitabine, an oral prodrug of 5-fluorouracil.

32 Claims, No Drawings

METHOD OF ORALLY TREATING INFLAMMATORY SKIN CONDITIONS WITH PRODRUGS OF 5-FLUOROURACIL

This application claims priority under 35 U.S.C. §119(e) to U.S. provisional patent application Ser. No. 60/419,231, filed Oct. 17, 2002. The entire contents of this provisional application is incorporated by reference.

FIELD OF THE INVENTION

The present invention relates to the oral administration of 5-fluorouracil (5-FU) prodrugs to treat inflammatory skin conditions. In a preferred embodiment, the invention relates to the oral administration of 5-FU prodrugs to treat psoriasis. In an especially preferred embodiment, the invention provides a treatment for psoriasis by oral administration of capecitabine.

BACKGROUND OF THE INVENTION

Psoriasis

Inflammatory skin conditions include psoriasis, keloid (hypertrophic scar), atopic dermatitis, lichen simplex chronicus, prurigo nodularis, Reiter syndrome, pityriasis rubra pilaris, pityriasis rosea, stasis dermatitis, rosacea, acne, lichen planus, scleroderma, seborrheic dermatitis, granuloma annulare, rheumatoid arthritis, dermatomyositis, alopecia areata, lichen planopilaris, vitiligo, and discoid lupus erythematosis. Psoriasis is a common skin condition with a prevalence of 1–2% in the general population. The disease is of undetermined etiology and affects patients of all ages with no gender preference. The most common presentation is plaque psoriasis, which is characterized by well-demarcated, erythematous plaques with scale on the extensor surfaces of the extremities, especially the elbows and knees, and the scalp. The plaques are highly vascularized and frequently bleed with mechanical removal of the scale (Auspitz sign). Histologically, the plaques have a characteristic epidermal hyperplasia with rete ridges hyper-extending in a regular fashion into the dermis and the intervening epidermis. The abnormal hyperplasia of the epidermis results in the characteristic scale due to incomplete terminal differentiation of keratinocytes. Neutrophils may also be typically found within the scale layers and may occasionally contribute to a pustular presentation. A lymphocyte predominant inflammatory infiltrate is present which is usually limited to the superficial plexus of blood vessels in the skin. (Dosik J, Shupack J *Current Dermatologic Diagnosis and Treatment*, edited by I M Reedberg and M R Sanchez. Philadelphia: Current Medicine Inc. 2001. pp.178–179).

Subcategories of psoriasis include pustular psoriasis, inverse psoriasis, guttate psoriasis, nail psoriasis, psoriatic arthritis, and exfoliative erythrodermic (Von Zumbusch) psoriasis. Pustular psoriasis is characterized by neutrophil predominance, pustule formation and sometimes systemic symptoms. Inverse psoriasis presents in intertriginous areas. Guttate psoriasis characteristics include a widespread presentation on the body, truncal lesions, small teardrop lesions, and eruptive lesions. Psoriatic arthritis is usually an asymmetric oligoarthritis. Exfoliative, or Von Zumbusch, psoriasis is a life threatening form. (see Dosik et al. supra).

The existing treatments for psoriasis are targeted at the major histopathologic components of the disease. Broad immunosuppression or T-lymphocyte specific immunosuppression is achieved by treatment with UVB, cyclosporine, methotrexate, topical steroids, and other immunosuppressive modalities. Keratinocyte terminal differentiation is targeted by calcipotriene and salicyclic acid. Retinoids target both immunosuppression and keratinocyte terminal differentiation. A drawback to many of the agents currently employed to treat psoriasis is that they must be administered by injection or in the hospital. Orally administered treatments have a better rate of patient compliance and are therefore preferable as compared to treatments that are administered via the intravenous route.

Oral treatments for inflammatory skin conditions are also preferable to topical treatments. Topical treatments are often ineffective because of washing or rubbing away from the affected area. Patients are inconvenienced by staining of clothes and furniture by topical treatments, and by the need to cover the affected area with occlusive or bulky dressings. Oral treatments have a better rate of patient compliance than topical treatments because they are more convenient. Orally administered treatments provide more reliable drug delivery because the problem of washing or rubbing away of topical treatments is avoided.

Poor efficacy and high recurrence rates are also common problems of existing treatments for psoriasis. Few treatments are rapid acting or cause the disease to become less severe for a time without absolutely ceasing. No existing treatment for psoriasis is both rapidly acting and causes the disease to become less severe for a time without absolutely ceasing. Existing treatments for other inflammatory skin conditions suffer from similar shortcomings.

5-fluorouracil 5-fluorouracil (5-FU) is a cytotoxic antimetabolite that is widely used against solid tumors including gastrointestinal, breast, and head and neck cancers. The efficacy of 5-FU in treating solid tumors is enhanced when 5-FU is used in combination with leucovorin, the calcium salt of folinic acid. (Malet-Martino M et al. Clinical Studies of Three Oral Prodrugs of 5-Fluorouracil (Capecitabine, UFT, S-1): A Review. *Oncologist* 2002;7(4)288–323).

5-FU is a known treatment for psoriasis. Administration is generally by intravenous catheter. The use of 5-FU is limited by its toxicity and its unpredictable bioavailability. The enzyme dihydropyrimidine dehydrogenase (DPD) deactivates more than 85% of the injected dose of 5-FU. The bioavailability of 5-FU is unpredictable, especially after oral administration. In some patients, where DPD has strong activity, little 5-FU is available. If DPD has weak activity then 5-FU levels are elevated, which may lead to toxicity from overdose. (Malet-Martino et al., supra).

Toxicities of 5-FU include myelosuppression, oral mucositis, diarrhea, nausea, vomiting, cardiotoxicity, and neurotoxicity. Continuous intravenous (IV) infusion of 5-FU may result in the hand-foot syndrome. (Malet-Martino et al., supra) Because of the possibility of severe toxic reactions, it is recommended that patients be hospitalized for, at least, their initial course of therapy with IV 5-FU. (*Physician's Desk Reference*, 56 edition 2002) The administration of 5-FU by protracted IV infusion is costly and is often associated with infectious and thrombotic complications related to the intravenous catheter. (de Bono J S, Twelves C J. The oral fluorinated pyrimidines. *Invest New Drugs* 2001; 19(1):41–59).

Because of the low effectiveness, side effects and toxicity of the existing treatments for inflammatory skin conditions, particularly psoriasis, there is a need in the art for an easily administered, efficacious and safe treatment for the disease.

Prodrugs

A prodrug is a pharmacologically inactive compound that is converted into a pharmacologically active agent by a metabolic transformation. In vivo, a prodrug is acted on by naturally occurring enzyme(s) resulting in liberation of the pharmacologically active agent. Prodrugs of 5-FU include capecitabine ($N^4$-pentyloxycarbonyl-5'-deoxy-5-fuorocytidine), 5-fluoro-pyrimidinone (5FP), TS-1 (S-1, ftorafur), FdUMP, 1-(2'-oxopropyl)-5FU, and alkyl-carbonyl-5-FU. Each 5-FU prodrug is enzymatically converted to 5-FU in the body.

Capecitabine

Capecitabine is a preferred 5-FU prodrug of the present invention. Capecitabine is known for use in the treatment of breast and colorectal cancer. Capecitabine has been studied for use in the treatment of advanced gastric cancer, non-small cell lung cancer and pancreatic cancer.

Capecitabine is customarily administered via the oral route, crosses the gastrointestinal barrier intact, and is rapidly and almost completely absorbed by humans. (Malet-Martino et al., supra) Capecitabine is converted into 5-FU in a three-stage process involving several enzymes. In the first step, capecitabine is metabolized to 5'-deoxy-5-fluorocytidine (5'-dFCR) by hepatic carboxylesterase. 5'-dFCR is deaminated to 5'd5-FUrd by cytidine deaminase. 5'd5-FUrd is transformed into 5-FU by thymidine phosphorylase (TP). TP has higher activity in tumor than in normal tissues. (Malet-Martino et al., supra) Capecitabine is preferentially converted to 5-FU at highly angiogenic sites in the body including psoriatic plaques. (Creamer D et al., Overexpression of the angiogenic factor platelet-derived endothelial growth factor/thymidine phosphorylase in psoriatic epidermis. *Br J Dermatol* December 1997) Capecitabine has an improved therapeutic index over 5-FU because capecitabine increases the concentration of the active principle at the tumor site with a resulting greater activity and decreases the concentration of drug in healthy tissues with a consequent reduction in systemic toxicity.

The most common toxicities of capecitabine are hand-foot syndrome and diarrhea. Other reported toxicities include mucositis, nausea, stomatitis, vomiting, alopecia, fatigue, leopard-like vitiligo, onychomadesis, and onycholysis.

Hand-foot syndrome is an adverse event that occurs more frequently with capecitabine than with 5-FU/leucovorin. Hand-foot syndrome occurred in 53% of patients treated with capecitabine versus 6% of patients treated with 5-FU/leucovorin. In the capecitabine group 17% of patients had the most severe form (grade 3) of hand-foot syndrome versus 1% of patients in the 5-FU/leucovorin group. (Malet-Martino et al., supra) TS-1 also induces hand-foot syndrome. (Elasmar SA et al. Case report: hand-foot syndrome induced by the oral fluorpyrimidine S-1. *Jpn J Clin Oncol* 2001 April; 31(4):172–4.).

Also known as palmar-plantar erythrodyesthesia, hand-foot syndrome results in painful reddening of the skin of the hands and feet in its mildest form, and in severe pain and loss of skin in its most severe form. The syndrome is graded on a scale between 1 and 3. Patients with Grade 1 disease experience numbness, dysesthesia, tingling, swelling, and erythema. Patients with Grade 2 disease experience painful erythema and swelling that affects activities of daily living. In Grade 3 disease, patients experience moist desquamation, ulceration, blistering, and severe pain that may result in inability to work or perform activities of daily living. (Blum J L et al. Multicenter phase II study of capecitabine in paclitaxel-refractory metastatic breast cancer. *J Clin Oncol* 1999; 17:485–493) Hand-foot syndrome initially starts with dysesthesia (an abnormal feeling of discomfort with weight bearing or touch) in the hands and feet, followed by edema and erythema, and ultimately, fissuring and ulceration involving the fingers, toes, palms and plantar aspects of the feet. As the syndrome progresses, the patient may experience extreme pain when grasping objects or walking. Hand-foot syndrome may also affect areas of the body other than the hands and feet, for example areas of the skin to which pressure is applied, such as at the belt or bra line. (Dorr et al. U.S. Pat. No. 6,060,083).

All references cited and discussed in this specification are incorporated herein by reference in their entirety.

SUMMARY OF THE INVENTION

The present invention provides a method for treating inflammatory skin conditions by orally administering an effective amount of a prodrug of 5-FU. The present invention additionally provides a method of treating psoriasis by orally administering an effective amount of an oral prodrug of 5-FU. In a preferred embodiment, the invention provides a method for treating psoriasis by oral administration of capecitabine. According to the invention an effective amount of capecitabine is orally administered to treat psoriasis.

DETAILED DESCRIPTION OF THE INVENTION

The present invention provides a method of treating inflammatory skin conditions, particularly psoriasis, by orally administering a prodrug of 5-FU. In a preferred embodiment, the present invention employs oral administration of capecitabine for treating psoriasis.

It has now been unexpectedly discovered that oral administration of 5-FU prodrugs can be used to treat psoriasis in humans. In a preferred embodiment, capecitabine (a 5-FU prodrug) is orally administered to treat psoriasis in humans. The 5-FU prodrugs that have been found to be useful for treatment of psoriasis in humans are capecitabine ($N^4$-pentyloxycarbonyl-5'-deoxy- 5-fuorocytidine), 5-fluoro-pyrimidinone (5FP), TS-1 (S-1, ftorafur), FdUMP, 1-(2'-oxopropyl)-5FU, and alkyl-carbonyl-5-FU.

The preferred 5-FU prodrug for use in the present invention is capecitabine. Capecitabine is a prodrug of the antimetabolite 5-FU, crosses the gastrointestinal barrier intact, and is rapidly and almost completely absorbed. Surprisingly, this drug, which is responsible for the skin disease known as hand-foot syndrome, is effective as a treatment for another skin disease, psoriasis. The effectiveness of capecitabine for the treatment of psoriasis is especially surprising because hand and foot syndrome (which involves erythema, pain and ulceration) and psoriasis may occur in the same area of the body. As an example, inverse psoriasis occurs in intertriginous areas, which are areas between folds or juxtaposed surfaces of skin. (Stedman's Medical Dictionary, $26^{th}$ edition) Intertriginous areas include the skin beneath pendulous breasts and abdominal skin folds. Hand-foot syndrome is known to occur at the intertriginous areas of the bra-line and belt-line. Moreover, pustular psoriasis is known to localize to the palms and soles. (Merck Manual of Diagnosis and Therapy, $17^{th}$ edition, section 10 ch. 117).

The use of capecitabine to treat psoriasis is a significant advance because it avoids the serious side effects of 5-FU. Furthermore, capecitabine can be reliably and effectively administered via the oral route. Most adverse events associated with capecitabine administration are reversible and do not require discontinuation of the drug. (Physician's Desk Reference, supra) A benefit of oral prodrugs of 5-FU, and capacitabine particularly, is that patients are more likely to initiate treatment if the active agent can be taken orally rather than undergo the additional pain, expense and inconvenience of IV treatment. Treatment with oral capecitabine does not require hospitalization as does initial IV therapy with 5-FU. (Malet-Martino et al., supra) In addition to the 5-FU specific toxicities, any intravenous catheterization carries the risk of local infection and/or thrombophlebitis. (de Bono J S, Twelves C J, supra).

The 5-FU prodrugs capecitabine ($N^4$-pentyloxycarbonyl-5'-deoxy-5-fuorocytidine), 5-fluoro-pyrimidinone (5FP), TS-1 (S-1, ftorafur), FdUMP, 1-(2'-oxopropyl)-5FU, and alkyl-carbonyl-5-FU can be orally administered to treat psoriasis and other inflammatory skin conditions (e.g., keloid (hypertrophic scar), atopic dermatitis, lichen simplex chronicus, prurigo nodularis, Reiter syndrome, pityriasis rubra pilaris, pityriasis rosea, stasis dermatitis, rosacea, acne, lichen planus, scleroderma, seborrheic dermatitis, granuloma annulare, rheumatoid arthritis, dermatomyositis, alopecia greata, lichen planopilaris, vitiligo, and discoid lupus erythematosis) in humans. Therapeutically effective oral doses of 5-FU prodrugs for treating psoriasis and other inflammatory skin conditions in humans in a non-pulse dosing regimen are between 5 and 2500 milligrams per square meter of body surface area per day, a preferred effective amount is between 100 and 1500 milligrams per square meter of body surface area per day and an especially preferred dose is 1250 milligrams per square meter of body surface area per day.

The preferred prodrug, capecitabine, is therapeutically effective for treating psoriasis and other inflammatory skin conditions in humans at doses below 2500 milligrams per square meter of body surface area per day, and capecitabine does not produce a 5-FU like adverse effect profile until dose levels exceed 2500 milligrams per square meter of body surface area per day. Adverse effects experienced at levels in excess of 2500 milligrams per square meter of body surface per day include nausea, vomiting and skin rashes. A therapeutically effective amount is that amount of capecitabine which will relieve or improve to some extent one or more of the symptoms or signs of psoriasis or other inflammatory skin condition.

An effective amount of capecitabine for treating psoriasis or other inflammatory skin condition in a non-pulse dosing regimen is between 100 and 2500 milligrams per square meter of body surface area per day, a preferred effective amount is between 750 and 1500 milligrams per square meter of body surface area per day and an especially preferred dose is 1250 milligrams per square meter of body surface area per day.

Capecitabine (offered under the brand name Xeloda® by Roche Labs, Nutley, N.J. 07110) is commercially available in 150 mg and 500 mg tablets. Xeloda® is indicated for the treatment of patients with metastatic breast cancer resistant to both paclitaxel and an anthracyline-containing chemotherapy regimen, or resistant to paclitaxel and for whom further anthracycline therapy is not indicated. (Physician's Desk Reference 2002) Peak plasma concentrations for capecitabine and its two main metabolites occur about 0.5 to 1.5 hours after administration. Plasma concentrations decline exponentially with a half-life of about 0.5 to 1 hour.

An additional dosing regimen is pulse-dosing. In pulse-dosing, an effective amount of a biologically active agent is administered to the patient and then sufficient time is allowed to permit the active agent to clear from the patient's body (i.e. to be metabolized or discharged) prior to the administration of additional doses. The quantity of drug administered to the patient in pulse-dosing may be greater than the dosage administered in a non-pulse-dosing regimen. The quantity, length of administration and interval between doses in pulse-dosing vary according to an individual patient's response to the pulse-dosing regimen.

An effective amount of oral 5-FU prodrug for treating psoriasis or other inflammatory skin condition by pulse dosing is between 5 and 5000 milligrams per square meter of body surface area, a preferred effective amount is between 100 and 3000 milligrams per square meter of body surface area and an especially preferred dose is 1250 milligrams per square meter of body surface area. A preferred pulse-dosing regimen is administration of the effective amount of the 5-FU prodrug daily for one week, an interval of two weeks without administration, repeat the schedule.

A preferred pulse-dosing regimen for treating psoriasis or other inflammatory skin condition is administering oral capecitabine in an effective amount between 100 and 5000 milligrams per square meter of body surface area, a preferred effective amount of between 750 and 3000 milligrams per square meter of body surface area and an especially preferred dose of 1250 milligrams per square meter of body surface area. In the pulse-dose regimen, the effective amount of capecitabine is administered orally each day for one week followed by an interval of one week without administration; the weekly cycle is repeated. Pulse-dose quantity, the period of time during which the effective amount is administered, and interval without dosing are adjusted for patient response and occurrence of adverse effects.

A 5-FU prodrug of the present invention is preferably administered as a pharmaceutical composition in hard shell dosage form such as a pill, tablet, capsule, or caplet. The pharmaceutical composition may be formulated as unit dosage forms, such as tablets, pills, capsules, boluses, powders, granules, elixirs, tinctures, metered aerosol or liquid sprays, drops, ampoules, autoinjector devices or suppositories. Unit dosage forms may be used for oral, intranasal, sublingual or rectal administration, or for administration by inhalation or insufflation, transdermal patches, and a lyophilized composition. Preferably the unit dosage form is an oral dosage form, most preferably a solid oral dosage, therefore the preferred dosage forms are tablets, pills, and capsules.

The pharmaceutical composition may contain capecitabine or an enantiomer, diastereomer, N-oxide, crystalline form, hydrate, solvate, active metabolite or pharmaceutically acceptable salt of the compound. The pharmaceutical composition may also include optional additives, such as a pharmaceutically acceptable carrier or diluent, a flavouring, a sweetener, a preservative, a dye, a binder, a suspending agent, a dispersing agent, a colorant, a disintegrator, an excipient, a diluent, a lubricant, an absorption enhancer, a bactericide and the like, a stabiliser, a plasticizer, an edible oil, or any combination of two or more of said additives.

Suitable pharmaceutically acceptable carriers or diluents include, but are not limited to, ethanol, water, glycerol, aloe vera gel, allantoin, glycerine, vitamin-A and E oils, mineral oil, phosphate buffered saline, PPG2 myristyl propionate, magnesium carbonate, potassium phosphate, vegetable oil, animal oil and solketal.

Suitable binders include, but are not limited to, starch, gelatine, natural sugars such as glucose, sucrose and lactose, corn sweeteners, natural and synthetic gums such as acacia, tragacanth, vegetable gum, sodium alginate, carboxymethylcellulose, polyethylene glycol, waxes and the like.

Suitable disintegrators include, but are not limited to, starch such as corn starch, methyl cellulose, agar, bentonite, xanthan gum and the like.

Suitable lubricants include, but are not limited to, sodium oleate, sodium stearate, magnesium stearate, sodium benzoate, sodium acetate, sodium chloride and the like.

Suitable suspending agents include, but are not limited to, bentonite.

Suitable dispersing and suspending agents include, but are not limited to, synthetic and natural gums such as vegetable gum, tragacanth, acacia, alginate, dextran, sodium carboxymethylcellulose, methylcellulose, polyvinylpyrrolidone and gelatine.

Suitable edible oils include, but are not limited to, cottonseed oil, sesame oil, coconut oil and peanut oil.

Examples of additional additives include, but are not limited to, sorbitol, talc, stearic acid and dicalcium phosphate.

Solid unit dosage forms may be prepared by mixing the active agents of the present invention with a pharmaceutically acceptable carrier and any other desired additives as described above. The mixture is typically mixed until a homogeneous mixture of the active agents of the present invention is obtained and the carrier and any other desired additives are formed, i.e. the active agents are dispersed evenly throughout the composition.

Tablets or pills can be coated or otherwise prepared so as to form a unit dosage form that has delayed and/or sustained action, such as controlled release and delayed release unit dosage forms. For example, the tablet or pill can comprise an inner dosage and an outer dosage component, the latter being in the form of a layer or envelope over the former. The two components can be separated by an enteric layer which serves to resist disintegration in the stomach and permits the inner component to pass intact into the duodenum or to be delayed in release.

Biodegradable polymers for controlling the release of the active agents include, but are not limited to, polylactic acid, polyepsilon caprolactone, polyhydroxybutyric acid, polyorthoesters, polyacetals, polydihydropyrans, polycyanoacrylates and crosslinked or amphipathic block copolymers of hydrogels.

For liquid dosage forms, the active substances or their physiologically acceptable salts are dissolved, suspended or emulsified, optionally with the usually employed substances such as solubilizers, emulsifiers or other auxiliaries. Solvents for the active combinations and the corresponding physiologically acceptable salts can include water, physiological salt solutions or alcohols, e.g. ethanol, propanediol or glycerol. Additionally, sugar solutions such as glucose or mannitol solutions may be used. A mixture of the various solvents mentioned may be used in the present invention too.

The active agents of the present invention may also be coupled with soluble polymers such as targetable drug carriers. Such polymers include, but are not limited to, polyvinylpyrrolidone, pyran copolymers, polyhydroxypropylmethacrylamidophenol, polyhydroxyethylaspartamidophenol, and polyethylenoxypolylysine substituted with palmitoyl residues.

A transdermal dosage form also is contemplated by the present invention. Transdermal forms may be a diffusion-driven transdermal system (transdermal patch) using either a fluid reservoir or a drug-in-adhesive matrix system. Other transdermal dosage forms include, but are not limited to, topical gels, lotions, ointments, transmucosal systems and devices, and iontohoretic (electrical diffusion) delivery system. Transdermal dosage forms may be used for timed release and sustained release of the active agents of the present invention.

The total daily dose should be taken as two divided doses approximately 12 hours apart, within 30 minutes of eating. The tablets should be taken with water. (Xeloda™ Patient Package Insert).

The number of daily tablets of a 5-FU prodrug to be taken by a patient for treatment of psoriasis or other inflammatory skin condition is shown in the following dosing table.

TABLE 1

Dosing table for 1250 milligrams per square of body surface area per day

| Dose level 1250 $(mg/m^2/day)$ Body surface area | Total daily dose | Number of tablets to be taken at each dose | |
|---|---|---|---|
| $(m^2)$ | (mg) | 150 mg tablet | 500 mg tablet |
| ≦1.41 | 1600 | 2 | 1 |
| 1.41–1.56 | 1900 | 3 | 1 |
| 1.57–1.72 | 2000 | 0 | 2 |
| 1.73–1.95 | 2300 | 1 | 2 |
| >1.95 | 2600 | 2 | 2 |

The Body Surface Area (BSA) is calculated using a BSA nomogram well known to those skilled in the art and the patient's height and mass. (Mosteller RD. Simplified calculation of body-surface area. *NEJM* 1987;317:1098). For any given BSA in the first column of Table 1, the total daily dose is disclosed in the second column of the table. The third and fourth columns of Table 1 show, respectively, the number of 150 milligram tablets and the number of 500 milligram tablets to be taken at each administration (morning and evening).

Duration of individual patient treatment will depend on individual response and tolerance. However, treatment with an effective amount of a 5-FU prodrug for 2 to 12 weeks should provide relief from psoriasis and other inflammatory skin conditions in most patients. The dosing regimen may be modified in the event of adverse events. An adverse event includes any adverse change from the patient's pre-treatment condition.

EXAMPLES

The following example is intended to illustrate more specifically the operation of the invention. The example is intended to illustrate and not to limit the scope of the invention. Other aspects, advantages and modifications within the scope of the invention will be apparent to those skilled in the art to which the invention pertains.

Example 1

Initiation of Treatment for Psoriasis with Capecitabine

Treatment of an adult with active psoriasis involving 10–75% body surface area (BSA) is carried out as follows. The physician obtains a complete medical history from the patient and conducts a physical examination. A Psoriasis Area and Severity Index (Fredriksson T, Petersson U, Severe psoriasis—oral therapy with a new retinoid. *Dermatologica* 1978;157:238–244), is obtained. A hematology profile (complete blood count and platelet count), chemistry profile (BUN, creatinine, SGOT, SGPT, total protein, and albumin), HIV screen, and urinalysis are also obtained. Women of child-bearing potential must have a negative serum pregnancy test within 7 days of the first dose of capecitabine.

The BSA is calculated using a BSA nomogram based on the patient's height and mass. A patient with a normal history, physical exam, blood and urine profiles is started on a course of capecitabine at 1250 milligrams per square meter of BSA per day according to Table 1. For example, a patient with a BSA of 1.50 square meters would receive a total daily dose of 1900 mg of capecitabine.

The patient is to take three 150 mg tablets and one 500 mg tablet with a glass of water within 30 minutes after eating breakfast. The same dose is repeated in the evening, approximately 12 hours later, with a glass of water within 30 minutes after dinner. The patient takes the daily dose for two days of the week and repeats this dosing schedule on the same days of the week on subsequent weeks.

From the foregoing disclosure it is evident that the present invention provides an advance in the treatment for psoriasis and inflammatory skin conditions. The present invention is preferably administered orally, which improves patient compliance with treatment and does not require hospitalization. Oral administration avoids the complications associated with intravenous catheterization. 5-FU prodrugs, preferably capecitabine, are effective for the treatment of psoriasis and other inflammatory skin conditions, and are safer than other drugs used for the treatment of psoriasis and other inflammatory skin conditions.

We claim:

1. A method for treating an inflammatory skin condition in a patient which consists essentially of orally administering an effective amount of a prodrug of 5-fluorouracil to said patient.

2. The method of claim 1 wherein the oral prodrug of 5-fluorouracil is selected from the group consisting of capecitabine, 5-fluoro-pyrimidinone, ftorafur (TS-1), FdUMP, 1-(2'-oxopropyl)-5-FU, and alkyl-carbonyl-5-FU.

3. The method of claim 1 wherein the inflammatory skin condition is selected from the group consisting of psoriais, keloid (hypertrophic scar), atopic dermatitis, lichen simplex chronicus, prurigo nodularis, Reiter syndrome, pityriasis rubra pilaris, pityriasis rosea, stasis dermatitis, rosacea, acne, lichen planus, scleroderma, seborrheic dermatitis, granuloma annulare, rheumatoid arthritis, dermatomyositis, alopecia areata, lichen planopilaris, vitiligo, and discoid lupus erythematosis.

4. The method of claim 1 which comprises administering the effective amount in a non-pulse dosing regimen.

5. The method of claim 4 wherein the effective amount in said non-pulse dosing regimen is between 5 and 2500 milligrams per square meter of body surface area per day.

6. The method of claim 4 wherein the effective amount in said non-pulse dosing regimen comprises between 100 and 1500 milligrams per square meter of body surface area per day.

7. The method of claim 4 wherein the effective amount in said non-pulse dosing regimen comprises 1250 milligrams per square meter of body surface area per day.

8. A method for treating psoriasis in a patient with psoriasis which consists essentially of orally administering an effective amount of a 5-fluorouracil prodrug to the patient.

9. The method of claim 8 wherein the oral prodrug of 5-fluorouracil is selected from the group consisting of capecitabine, 5-fluoro-pyrimidinone, ftorafur (TS-1), FdUMP, 1-(2'-oxopropyl)-5FU, and alkyl-carbonyl-5-FU.

10. The method of claim 8 which comprises administering the effective amount in a non-pulse dosing regimen.

11. The method of claim 10 wherein said effective amount in said non-pulse dosing regimen is between 5 and 2500 milligrams per square meter of body surface area per day.

12. The method of claim 10 wherein the effective amount in said non-pulse dosing regimen comprises between 100 and 1500 milligrams per square meter of body surface area per day.

13. The method of claim 10 wherein the effective amount in said non-pulse dosing regimen comprises 1250 milligrams per square meter of body surface area per day.

14. The method of claim 10 wherein the oral prodrug is capecitabine.

15. The method of claim 14 which comprises administering capecitabine to a patient in need of such treatment.

16. The method of claim 14 wherein the effective amount in said non-pulse-dosing regimen comprises between 5 and 2500 milligrams per square meter of body surface area per day.

17. The method of claim 14 wherein the effective amount in said non-pulse-dosing regimen comprises between 100 and 1500 milligrams per square meter of body surface area per day.

18. The method of claim 14 wherein the effective amount in said non-pulse-dosing regimen comprises 1250 milligrams per square meter of body surface area per day.

19. The method of claim 1 which comprises administering an oral prodrug of 5-fluorouracil by pulse-dosing.

20. The method of claim 19 wherein the effective amount by pulse dosing comprises between 5 and 5000 milligrams per square meter of body surface area per day.

21. The method of claim 19 wherein the effective amount comprises between 100 and 3000 milligrams per square meter of body surface area per day.

22. The method of claim 19 wherein the effective amount comprises 1250 milligrams per square meter of body surface area per day.

23. The method of claim 19 which comprises administering capecitabine by pulse-dosing.

24. The method of claim 23 wherein the effective amount of capecitabine comprises between 100 and 5000 milligrams per square meter of body surface area per day.

25. The method of claim 23 wherein the effective amount of capecitabine comprises between 750 and 3000 milligrams per square meter of body surface area per day.

26. The method of claim 23 wherein the effective amount of capecitabine comprises 1250 milligrams per square meter of body surface area per day.

27. A method of treating an inflammatory skin condition in a patient with an inflammatory skin condition which consists essentially of administering an effective amount of a transdermal prodrug of 5-fluorouracil to the patient.

28. A method of treating an inflammatory skin condition in a patient with an inflammatory skin condition which consists essentially of administering an effective amount of a transmucosal prodrug of 5-fluorouracil to the patient.

29. The method of claim 28 wherein the transmucosal prodrug is administered rectally.

30. A method for treating an inflammatory skin condition in a patient with an inflammatory skin condition, which comprises orally administering an effective amount of capecitabine to the patient.

31. The method of claim 30, wherein the inflammatory skin condition is psoriasis.

32. A method of treating an inflammatory skin condition in a patient with an inflammatory skin condition, which comprises transdermally or transmucosally administering an effective amount of capecitabine to the patient.

* * * * *